US00PP09186P

United States Patent [19]

Van Der Meer

[11] Patent Number: Plant 9,186

[45] Date of Patent: Jul. 4, 1995

[54] HYBRID TEA ROSE PLANT NAMED 'SELCARBONIUM'

[75] Inventor: Peter J. A. Van Der Meer, Carlsbad, Calif.

[73] Assignee: Terra Nigra B.V., De Kwakel, Netherlands

[21] Appl. No.: 105,359

[22] Filed: Aug. 11, 1993

[30] Foreign Application Priority Data

Sep. 21, 1992 [NL] Netherlands ..... ROO 1854

[51] Int. Cl.[6] ..... A01H 5/00

[52] U.S. Cl. ..... Plt./18

[58] Field of Search ..... Plt. 14, 18, 11

*Primary Examiner*—Howard J. Locker

[57] ABSTRACT

A new rose variety of the Hybrid Tea class, characterized by its continuous and profuse production of large cream with a pink hue flowers, borne singly on upright stems on a sturdy bush of medium height, having abundant foliage and a distinct fragrance.

2 Drawing Sheets

BACKGROUND OF THE INVENTION

The present invention relates to a new and distinct variety of rose plant of the Hybrid Tea class, which was originated by me by crossing the variety "Tineke" (U.S. Plant Pat. No. 8,055) with an unnamed (SR 85.076) and unpatented seedling. Tineke differs from "Selcarbonium" by its whiter flower color, larger petal count, longer stems, weaker fragrance, and lower flower production.

The primary objective of this breeding was to obtain a new rose variety comparable to that of "Tineke", but with a strong fragrance. While the results achieved a distinctive fragrant hybrid tea rose of large size, the new variety did not otherwise correspond to the characteristics of "Tineke", but nevertheless, achieved a new and distinct combination of characteristics which is desirable and attractive, as well as different from anything heretofore available, as evidenced by the following characteristics which are outstanding in the new variety:

(1) a large cream/very soft pink flower
(2) rapid flowering cycles
(3) distinctive fragrance
(4) a vigorous upright plant of medium height.

The foregoing characteristics and distinctions definitely differentiate the new variety from its parents, as well as from all other varieties of which I am aware, and asexual reproduction of the new variety by cuttings, grafting or tissue culture as performed in a greenhouse in De Kwakel, the Netherlands, shows that these and all other characteristics and distinctions come true to form and are established and transmitted through succeeding propagations.

BRIEF DESCRIPTION OF THE DRAWINGS

The new variety of rose plant is illustrated by the accompanying photographic illustrations, of which Sheet 1 shows a full face view of the flower and Sheet 2 shows typical specimens of the vegetative growth and flowers of the new variety in different stages of development. The color renditions are as nearly true as it is possible to make same in color illustrations of this character by conventional photographic procedures. In this regard, the bloom coloration depicted in Sheet 1 is notably lighter than true bloom coloration.

The following is a detailed description of this new variety, with color terminology in accordance with the Royal Horticultural Society Colour Chart (RHSCC). The terminology used in the color description herein refers to plate numbers in the aforementioned color chart e.g. "53A" is plate "53A of the Royal Horticultural Society Colour Chart.

Parentage: Seedling.

*Seed parent.*—"Tineke".

*Pollen parent.*—Unnamed seedling (SR 85.076).

Classification:

*Botanic.*—Hybrid Tea.

*Commercial.*—Hybrid Tea.

BOTANICAL DESCRIPTION OF THE PLANT

FLOWER (Observations made from specimens grown in a greenhouse at De Kwakel, the Netherlands)

Blooming habit of Selcarbonium: Recurrent-continuous.

A. Bud:

(1) *Size.*—Large. Diameter 2.0–2.5 cm. Length 3.0–3.5 cm.

(2) *Form.*—Egg shaped (oval, pointed;) is not affected by wet or hot weather.

(3) *Color.*—When the sepals first divide, the color of the outside is white 157C with some green 139C–138A with pink edge 56B.

(4) Sepals.—Slightly branched, curl back when petals begin to unfurl. Color: inside: green 138B. outside: green 143A.

(5) *Calyx.*—Color: green 142B. Shape: funnel. Size: large. Aspect: smooth. Odor when rubbed: none.

(6) *Peduncle.*—Length: long, 10 cm. Aspect: smooth. Strength: medium. Color: medium green 143B.

(7) *Openings.*—Opens up well: is not affected by adverse weather.

B. Bloom:

(1) *Size.*—Large; when fully expanded about 12 cm in diameter with a depth of about 6 cm.

(2) *Borne.*—Single.

(3) *Stems.*—Average length, average strength.

(4) *Form (when first open).*—Cup-form. Permanence: will flatten when aging.

(5) *Petalage.*—Number of petals: 25–29.

(6) *Color.*—Center of flower: light purple (65D). Outer petals: white (155C). Base of petals: light purple (65D). Inside of petals: white (155C) and light purple (65). Reverse of petals: white with some very soft purple (155C-65D) and some green stripes (144A). General tonality: white with very soft purple (155C-65D) and some green (144A).

(7) *Discoloration.*—General tonality at end of first day: white and light purple (155C-65D). Second day: same; white and light purple (155C-65D). Third day: same; white and light purple (155C-65D), but the purple has faded).

C. Petals:

(1) *Texture.*—Soft; not affected by wet or hot weather.

(2) *Appearance.*—Inside: satiny. Outside: shiny.

(3) *Form.*—Heart shaped.

(4) *Arrangement.*—Regular informal.

(5) *Petaloids in center.*—few; large.

(6) *Persistence.*—Drop off cleanly.

(7) *Fragrance.*—A distinctive and fresh lemon-like scent.

(8) *Lasting quality.*—On the plant — long. As cut flower — reasonably long for a fragrant rose (7 days).

REPRODUCTIVE ORGANS

Stamens, anthers:

*Size,.*—Medium; regularly arranged around styles, average number about 190.

*Color.*—Orange-yellow.

Stamens, filaments (threads); Long, average about 8 to 10 mm in length.

*Color.*—Pink to light red-purple.

Pollen:

*Color.*—Orange-yellow.

Styles: Bunched; uneven length; medium about (5–6 mm) length; thin.

Stigmas:

*Color.*—White.

Ovaries: All enclosed in calyx; wedge-shaped.

Hips/Seeds: Seeds are produced both within the hips and they protrude from the top; hips are pear-shaped and orange at maturity.

Resistancy: Normal resistance against mildew, white fly, Californian thrips; red spider mites.

PLANT

Form: Upright and branched.

Growth; Vigorous; upright; medium height, average height after one year is 80–100 cm.

Foliage: Compound of 3,5 or 7 leaflets; average leaflet length is about 4.5 to 7.5 cm; average size of compound leaf is about 13 cm in length; average of 6–8 leaves on main canes.

(1) *Size.*—Large.

(2) *Quantity.*—Abundant.

(3) *Color.*—New foliage. upper side — green 137B. under side — green 138C. Old foliage: upper side — green 137B. under side — green 138C.

(4) *Shape.*—Oval, pointed.

(5) *Texture.*—Upper Side — smooth and slightly glossy. under side — smooth and dull.

(6) *Ribs and veins.*—Ordinary.

(7) *Edge.*—Serrated, saw toothed.

(8) *Serration.*—Single.

(9) *Leaf stem.*—Color: green 143B. under side: smooth; underside may occasionally have some small prickles about 1.5 mm in length.

(10) *Stipules.*—Medium length; smooth.

Wood:

*New wood.*—Color: bronze. Bark: smooth.

*Old wood.*—Color: green. Bark: smooth.

Thorns:

*Quantity.*—On main stalks from base: average; the upper part of the stem is almost thornless; the lower part of the stem has an average of about 3–5 thorns per 10 cm stem length. On laterals from stalk: average. Form: concave. Length: medium. Hooked: downward. Color (when young): yellow green. Position: irregular.

Prickles:

*Quantity.*—On main stalks: average. On laterals: average.

Short needles:

*Quantity.*—On main stalks: none. On laterals: none.

I claim:

1. A new and distinct variety of rose plant of the Hybrid Tea class, substantially as herein shown and described, and characterized by its large cream colored flowers which exhibit a very soft pink hue and which are borne singly, its distinct fragrance, and its rapid flowering cycles.

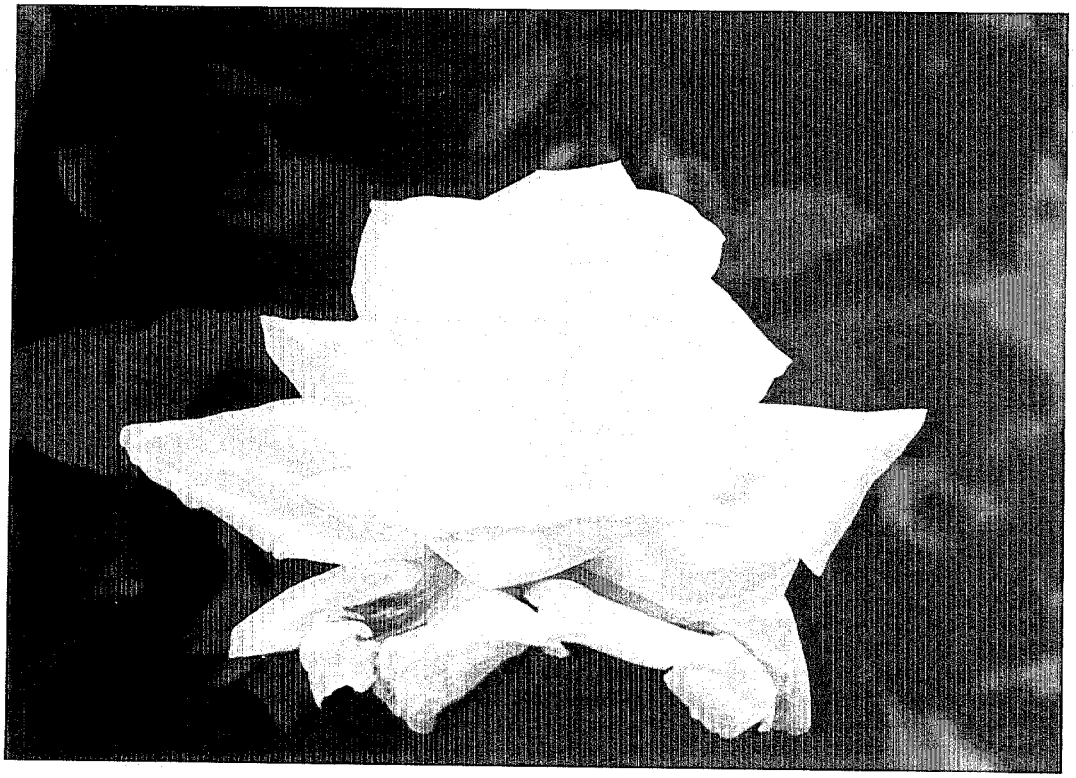

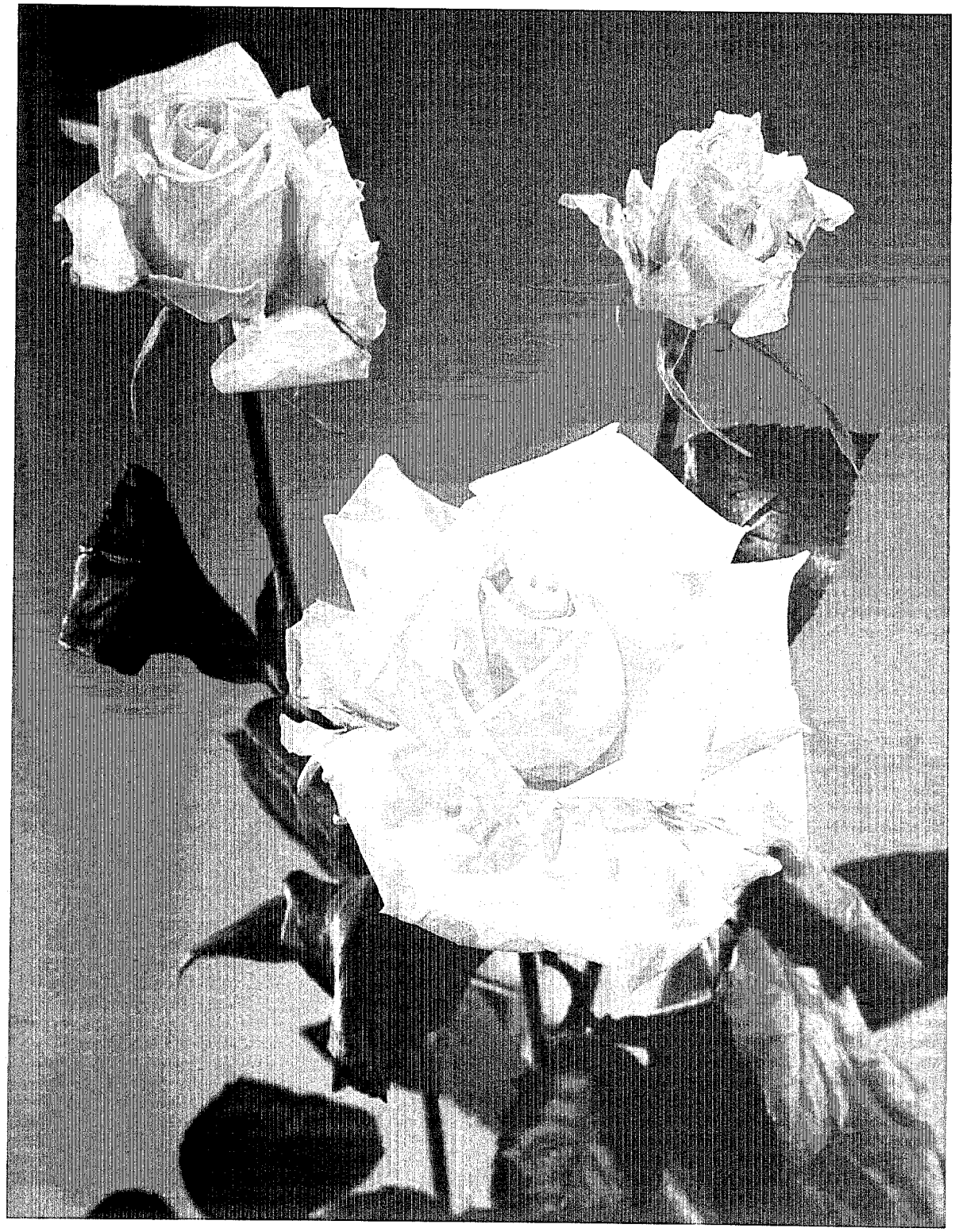

* * * * *